(12) United States Patent
Bille et al.

(10) Patent No.: US 8,366,701 B2
(45) Date of Patent: Feb. 5, 2013

(54) SYSTEM AND METHOD FOR CORRECTING HIGHER ORDER ABERRATIONS WITH CHANGES IN INTRASTROMAL BIOMECHANICAL STRESS DISTRIBUTIONS

(75) Inventors: Josef F. Bille, Heidelberg (DE); Frieder Loesel, Mannheim (DE); Luis Antonio Ruiz, Bogotá (CO)

(73) Assignee: Technolas Perfect Vision GmbH, Munich (DE)

( * ) Notice: Subject to any disclaimer, the term of this patent is extended or adjusted under 35 U.S.C. 154(b) by 1046 days.

(21) Appl. No.: 12/360,715

(22) Filed: Jan. 27, 2009

(65) Prior Publication Data

US 2010/0191227 A1    Jul. 29, 2010

(51) Int. Cl.
A61B 18/18    (2006.01)

(52) U.S. Cl. .......................................................... 606/5

(58) Field of Classification Search .................. 128/898; 606/4–6
See application file for complete search history.

(56) References Cited

U.S. PATENT DOCUMENTS

| | | | |
|---|---|---|---|
| 4,309,998 A | 1/1982 | Aron nee Rosa et al. | |
| 4,391,275 A | 7/1983 | Fankhauser et al. | |
| 4,669,466 A | 6/1987 | L'Esperance | |
| 4,718,418 A | 1/1988 | L'Esperance, Jr. | |
| 4,721,379 A | 1/1988 | L'Esperance | |
| 4,732,148 A | 3/1988 | L'Esperance, Jr. | |
| 4,770,172 A | 9/1988 | L'Esperance, Jr. | |
| 4,887,592 A | 12/1989 | Loertscher | |
| 4,907,586 A | 3/1990 | Bille et al. | |
| 4,941,093 A | 7/1990 | Marshall et al. | |
| 4,988,348 A | 1/1991 | Bille | |
| 5,549,632 A | 8/1996 | Lai | |
| 5,984,916 A | 11/1999 | Lai | |
| 5,993,438 A | 11/1999 | Juhasz et al. | |
| 6,110,166 A | 8/2000 | Juhasz | |
| 6,245,059 B1 | 6/2001 | Clapham | |
| 6,325,792 B1 | 12/2001 | Swinger et al. | |
| 6,610,050 B2 * | 8/2003 | Bille ................................ | 606/5 |
| 6,610,051 B2 | 8/2003 | Bille | |
| 6,635,051 B1 * | 10/2003 | Hohla ............................... | 606/5 |
| 6,648,877 B1 * | 11/2003 | Juhasz et al. ..................... | 606/5 |
| 6,730,074 B2 * | 5/2004 | Bille et al. ......................... | 606/5 |
| 2004/0044355 A1 | 3/2004 | Nevyas | |
| 2005/0149005 A1 * | 7/2005 | Bille ................................ | 606/5 |

(Continued)

FOREIGN PATENT DOCUMENTS

| | | |
|---|---|---|
| EP | 1252872 A1 | 10/2002 |
| EP | 1364632 A1 | 11/2003 |

(Continued)

*Primary Examiner* — Ryan Severson
*Assistant Examiner* — David Eastwood
(74) *Attorney, Agent, or Firm* — Nydegger & Associates

(57) ABSTRACT

A method for correcting higher order aberrations in an eye requires Laser Induced Optical Breakdown (LIOB) of stromal tissue. In detail, the method identifies at least one volume of stromal tissue in the eye, with each volume defining a central axis parallel to the visual axis of the eye. Thereafter, a pulsed laser beam is focused to a focal spot in each volume of stromal tissue to cause LIOB of stromal tissue at the focal spot. Further, the focal spot is moved through the volume of stromal tissue to create a plurality of incisions centered about the respective central axis of the volume. As a result, a predetermined selective weakening of the stroma is caused for correction of the higher order aberration.

8 Claims, 3 Drawing Sheets

U.S. PATENT DOCUMENTS

| | | | |
|---|---|---|---|
| 2005/0149006 A1* | 7/2005 | Peyman | 606/5 |
| 2005/0165386 A1* | 7/2005 | Kurtz et al. | 606/4 |
| 2007/0219543 A1 | 9/2007 | Yee | |
| 2008/0039825 A1* | 2/2008 | Lai | 606/5 |
| 2008/0065052 A1* | 3/2008 | Bischoff et al. | 606/4 |
| 2008/0287935 A1* | 11/2008 | Bille | 606/11 |
| 2009/0157061 A1* | 6/2009 | Ruiz et al. | 606/5 |
| 2009/0157063 A1* | 6/2009 | Ruiz et al. | 606/5 |
| 2009/0187171 A1* | 7/2009 | Loesel et al. | 606/5 |
| 2010/0217247 A1* | 8/2010 | Bille et al. | 606/5 |

FOREIGN PATENT DOCUMENTS

| | | |
|---|---|---|
| EP | 1473006 A1 | 11/2004 |

\* cited by examiner

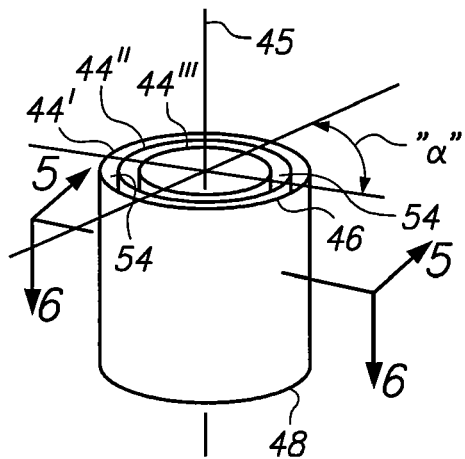
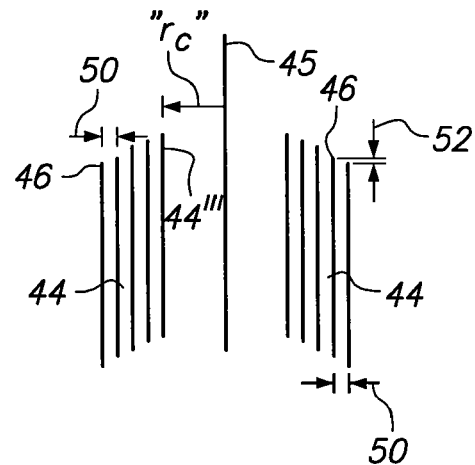
FIG. 4  FIG. 5
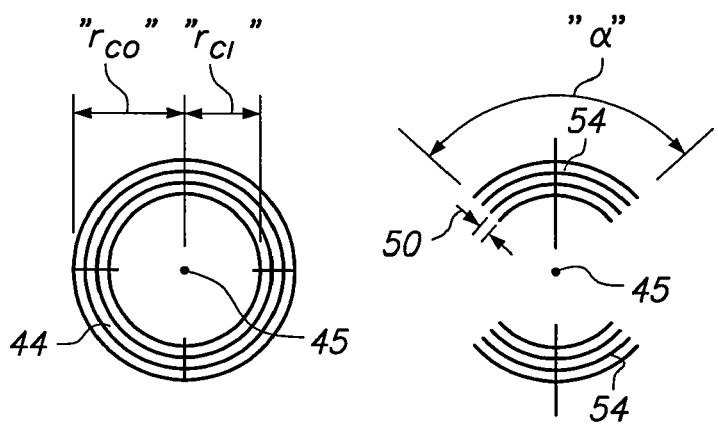
FIG. 6A  FIG. 6B  FIG. 6C

SYSTEM AND METHOD FOR CORRECTING HIGHER ORDER ABERRATIONS WITH CHANGES IN INTRASTROMAL BIOMECHANICAL STRESS DISTRIBUTIONS

FIELD OF THE INVENTION

The present invention pertains generally to methods for performing intrastromal ophthalmic laser surgery. More particularly, the present invention pertains to laser surgery to correct higher order aberrations in an eye. The present invention is particularly, but not exclusively, useful as a method for correcting higher order aberrations in an eye wherein incisions centered about a plurality of axes parallel to the visual axis cause a predetermined selective weakening of the stroma via changes in intrastromal biomechanical stress distributions.

BACKGROUND OF THE INVENTION

The cornea of an eye has five (5) different identifiable layers of tissue. Proceeding in a posterior direction from the anterior surface of the cornea, these layers are: the epithelium; Bowman's capsule (membrane); the stroma; Descemet's membrane; and the endothelium. Behind the cornea is an aqueous-containing space called the anterior chamber. Importantly, pressure from the aqueous in the anterior chamber acts on the cornea with bio-mechanical consequences. Specifically, the aqueous in the anterior chamber of the eye exerts an intraocular pressure against the cornea. This creates stresses and strains that place the cornea under tension.

Structurally, the cornea of the eye has a thickness (T) that extends between the epithelium and the endothelium. Typically, "T" is approximately five hundred microns (T=500 μm). From a bio-mechanical perspective, Bowman's capsule and the stroma are the most important layers of the cornea. Within the cornea, Bowman's capsule is a relatively thin layer (e.g. 20 to 30 μm) that is located below the epithelium, within the anterior one hundred microns of the cornea. The stroma then comprises almost all of the remaining four hundred microns in the cornea. Further, the tissue of Bowman's capsule creates a relatively strong, elastic membrane that effectively resists forces in tension. On the other hand, the stroma comprises relatively weak connective tissue.

Bio-mechanically, Bowman's capsule and the stroma are both significantly influenced by the intraocular pressure that is exerted against the cornea by aqueous in the anterior chamber. In particular, this pressure is transferred from the anterior chamber, and through the stroma, to Bowman's membrane. It is known that how these forces are transmitted through the stroma will affect the shape of the cornea. Thus, by disrupting forces between interconnective tissue in the stroma, the overall force distribution in the cornea can be altered. Consequently, this altered force distribution will then act against Bowman's capsule. In response, the shape of Bowman's capsule is changed, and due to the elasticity and strength of Bowman's capsule, this change will directly influence the shape of the cornea.

It is well known that all of the different tissues of the cornea are susceptible to LIOB. Further, it is known that different tissues will respond differently to a laser beam, and that the orientation of tissue being subjected to LIOB may also affect how the tissue reacts to LIOB. With this in mind, the stroma needs to be specifically considered.

The stroma essentially comprises many lamellae that extend substantially parallel to the anterior surface of the eye. In the stroma, the lamellae are bonded together by a glue-like tissue that is inherently weaker than the lamellae themselves. Consequently, LIOB over layers parallel to the lamellae can be performed with less energy (e.g. 0.8 μJ) than the energy required for the LIOB over cuts that are oriented perpendicular to the lamellae (e.g. 1.2 μJ). It will be appreciated by the skilled artisan, however, that these energy levels are only exemplary. If tighter focusing optics can be used, the required energy levels will be appropriately lower. In any event, depending on the desired result, it may be desirable to make only cuts in the stroma. On the other hand, for some procedures it may be more desirable to make a combination of cuts and layers.

As implied above, reshaping of the cornea by weakening tissue in the stroma can be an effective way to provide refractive corrections that will improve a vision defect. Not all vision defects, however, are caused by aberrations that are symmetrical with respect to the visual axis. Indeed, the higher order aberrations are typically asymmetrical. Accordingly, it may be necessary to weaken tissue in volumes that are offset from the visual axis. With all of this in mind, and as intended for the present invention, refractive surgery is accomplished by making incisions in the stroma centered about axes parallel to the visual axis to induce a redistribution of bio-mechanical forces that will reshape the cornea.

In light of the above, it is an object of the present invention to provide methods for correcting higher order aberrations through changes in intrastromal biomechanical stress distributions for improvement of a patient's vision. Another object of the present invention is to provide methods for correcting higher order aberrations that require minimal LIOB of stromal tissue. Still another object of the present invention is to provide methods for performing ophthalmic laser surgery that create incisions having a same pattern at selected locations about the visual axis. Yet another object of the present invention is to provide methods for correcting higher order aberrations via ophthalmic laser surgery that are relatively easy to implement and comparatively cost effective.

SUMMARY OF THE INVENTION

In accordance with the present invention, methods for correcting higher order aberrations in an eye via intrastromal ophthalmic laser surgery are provided that cause the cornea to be reshaped under the influence of intrastromal bio-mechanical stress distributions. Importantly, for these methods, at least one volume of stromal tissue is identified for operation. Structurally, each operational volume extends posteriorly from about ten microns below Bowman's membrane to a substantial depth into the stroma that is about 150 microns from the endothelium. Further, each operational volume defines a central axis that is parallel to and located at a distance from the visual axis of the eye.

In general, the method of the present invention requires the use of a laser unit that is capable of generating a so-called pulsed, femtosecond laser beam. Stated differently, the duration of each pulse in the beam will approximately be less than one picosecond. When generated, this beam is focused onto a focal spot in the volume of stromal tissue. The well-known result of this is a Laser Induced Optical Breakdown (LIOB) of stromal tissue at the focal spot. In particular, and as intended for the present invention, movement of the focal spot within each volume of stromal tissue creates a plurality of incisions that are centered about the respective central axis of the volume. The purpose here is to cause a predetermined selective weakening of the stroma for correction of the higher order aberration. Preferably, each incision has a same pattern. For purposes of the present invention, "incision" may refer to a location of weakened or eliminated tissue along the path of the focal point.

In certain embodiments, various volumes of stromal tissue with corresponding central axes are identified. For each embodiment, the central axes are arranged equidistant from the visual axis. Geometrically, the respective incisions may form concentric cylinders that are centered on the respective central axis. Other incision shapes may, however, be used. For example, the incisions may be concentric cylinder sections centered on the central axis, or they may be rectangular cylinders centered on the central axis, or they may be crosses that are centered on the central axis. In certain embodiments, the incisions will each have a thickness of about two microns.

In accordance with the present invention, various procedures can be customized to treat identifiable refractive imperfections. Specifically, in addition to specific incisions alone, the present invention contemplates using combinations of various types of incisions. In each instance, the selection of incisions will depend on how the cornea needs to be reshaped.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4 is a perspective view of a plurality of cylindrical surfaces where laser incisions can be made by LIOB;

FIG. 5 is a cross-sectional view of incisions on the plurality of cylindrical surfaces, as seen along the line 5-5 in FIG. 4, with the incisions shown for a typical treatment of presbyopia;

FIG. 6A is a cross-sectional view of the plurality of cylindrical surfaces as seen along the line 6-6 in FIG. 4 when complete incisions have been made on the cylindrical surfaces;

FIG. 6B is a cross-sectional view of the plurality of cylindrical surfaces as seen along the line 6-6 in FIG. 4 when partial incisions have been made along arc segments on the cylindrical surfaces for the treatment of astigmatism;

FIG. 6C is a cross-sectional view of an alternate embodiment for incisions made similar to those shown in FIG. 6B and for the same purpose;

DESCRIPTION OF THE PREFERRED EMBODIMENTS

Figure 1:
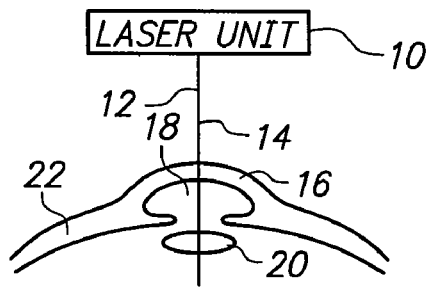
FIG. 1 is a cross-sectional view of the cornea of an eye shown in relationship to a schematically depicted laser unit.

Referring initially to FIG. 1, it will be seen that the present invention includes a laser unit 10 for generating a laser beam 12. More specifically, the laser beam 12 is preferably a pulsed laser beam, and the laser unit 10 generates pulses for the beam 12 that are less than one picosecond in duration (i.e. they are femtosecond pulses). In FIG. 1, the laser beam 12 is shown being directed along the visual axis 14 and onto the cornea 16 of the eye. Also shown in FIG. 1 is the anterior chamber 18 of the eye that is located immediately posterior to the cornea 16. There is also a lens 20 that is located posterior to both the anterior chamber 18 and the sclera 22.

Figure 2:
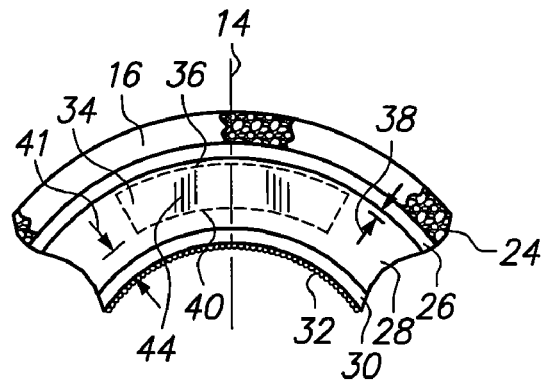
FIG. 2 is a cross-sectional view of the cornea showing a defined operational volume in accordance with the present invention.

In FIG. 2, five (5) different anatomical tissues of the cornea 16 are shown. The first of these, the epithelium 24 defines the anterior surface of the cornea 16. Behind the epithelium 24, and ordered in a posterior direction along the visual axis 14, are Bowman's capsule (membrane) 26, the stroma 28, Descemet's membrane 30 and the endothelium 32. Of these tissues, Bowman's capsule 26 and the stroma 28 are the most important for the present invention. Specifically, Bowman's capsule 26 is important because it is very elastic and has superior tensile strength. It therefore, contributes significantly to maintaining the general integrity of the cornea 16.

For the methods of the present invention, Bowman's capsule 26 must not be compromised (i.e. weakened). On the other hand, the stroma 28 is intentionally weakened. In this case, the stroma 28 is important because it transfers intraocular pressure from the aqueous in the anterior chamber 18 to Bowman's membrane 26. Any selective weakening of the stroma 28 will therefore alter the force distribution in the stroma 28. Thus, as envisioned by the present invention, LIOB in the stroma 28 can be effectively used to alter the force distribution that is transferred through the stroma 28, with a consequent reshaping of the cornea 16. Bowman's capsule 26 will then provide structure for maintaining a reshaped cornea 16 that will effectively correct refractive imperfections.

While referring now to FIG. 2, it is to be appreciated that an important aspect of the present invention is the identification of operational volumes 34 which are defined in the stroma 28. Although the operational volumes 34 are shown in cross-section in FIG. 2, they are actually three-dimensional, and extends from an anterior surface 36 that is located at a distance 38 below Bowman's capsule 26, to a posterior surface 40 that is located at a distance 41 from the endothelium 32. Both the anterior surface 36 and the posterior surface 40 essentially conform to the curvature of the stroma 28. For a more exact location of the anterior surface 36 of the operational volumes, the distance 38 will be about ten microns. For the posterior surfaces 40, the distance 41 will be about one-hundred-fifty microns.

Figure 3:
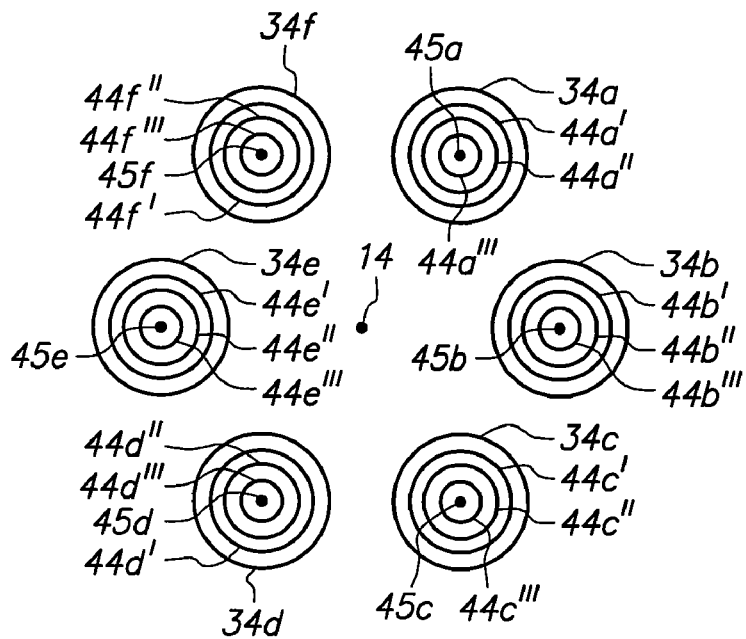
FIG. 3 is a front view of a stroma centered on the visual axis and illustrating a plurality of operational volumes, with each operational volume having a plurality of incisions.

In FIG. 3, incisions 44a-44f are made in a plurality of operational volumes 34a-34f as envisioned for the present invention. Although six different volumes 34a-34f are shown in FIG. 3 (also FIGS. 6D and 6E) it will be appreciated by the skilled artisan, this is only exemplary and presented here for purposes of disclosure. More specifically, for third order aberrations only three volumes 34 need to be identified. In any event, the exact number of volumes 34, and their respective radial distances from the visual axis 14 for any specific higher order aberration can be ascertained from the well known Zernike polynomials. As shown, for each operational volume 34a-34f, a plurality of incisions 44', 44" and 44''' are made, though there may be more or fewer incisions 44, depending on the needs of the particular procedure. With this in mind, and for purposes of this disclosure, the plurality in a selected volume 34 will sometimes be collectively referred to as incisions 44. Further, as shown in FIG. 3, six operational volumes have been identified. However, any number of operational volumes 34 may be used for the present invention.

As shown in FIG. 3, the exemplary incisions 44 for each operational volume 34 are made on respective cylindrical surfaces. Although the incisions 44 are shown as circular cylindrical surfaces, these surfaces may be oval. When the plurality of incisions 44 is made in the stroma 28, it is absolutely essential that it be confined within the respective operational volume 34. With this in mind, it is envisioned that incisions 44 will be made by a laser process using the laser unit 10. And, that this process will result in Laser Induced Optical Breakdown (LIOB). Further, in the illustrated embodiment, it is important these cylindrical surfaces be concentric, and that they are centered on a respective central axis 45a-45f distanced from and parallel to the visual axis 14.

Cross-referencing FIG. 3 with FIGS. 4 and 5, it can be seen that each incision 44 has an anterior end 46 and a posterior end 48. Further, the incisions 44 (i.e. the circular or oval cylindrical surfaces) have a spacing 50 between adjacent incisions 44. Preferably, this spacing 50 is equal to approximately two hundred microns. FIG. 5 also shows that the anterior ends 46 of respective individual incisions 44 can be displaced axially from each other by a distance 52. Typically, this distance 52 will be around ten microns. Further, the innermost incision 44 (e.g. incision 44''' shown in FIG. 4) will be at a radial distance "$r_c$" that will be about 1 millimeter from the central axis 45. From another perspective, FIG. 6A shows the incisions 44 centered on the central axis 45 to form a plurality of rings. In this other perspective, the incisions 44 collectively establish an inner radius "$r_{ci}$" and an outer radius "$r_{co}$". Preferably, each incision 44 will have a thickness of about two microns, and the energy required to make the incision 44 will be approximately 1.2 microJoules.

As an alternative to the incisions 44 disclosed above, FIG. 4 indicates that only arc segments 54 may be used, if desired. Specifically, in all essential respects, the arc segments 54 are identical with the incisions 44. The exception, however, is that they are confined within diametrically opposed arcs identified in FIGS. 4 and 6B by the angle "α". More specifically, the result is two sets of diametrically opposed arc segments 54. Preferably, "α" is in a range between five degrees and one hundred and sixty degrees.

An alternate embodiment for the arc segments 54 are the arc segments 54' shown in FIG. 6C. There it will be seen that the arc segments 54' like the arc segments 54 are in diametrically opposed sets. The arc segments 54', however, are centered on respective axes (not shown) that are parallel to each other, and equidistant from the central axis 45.

Figure 6D:
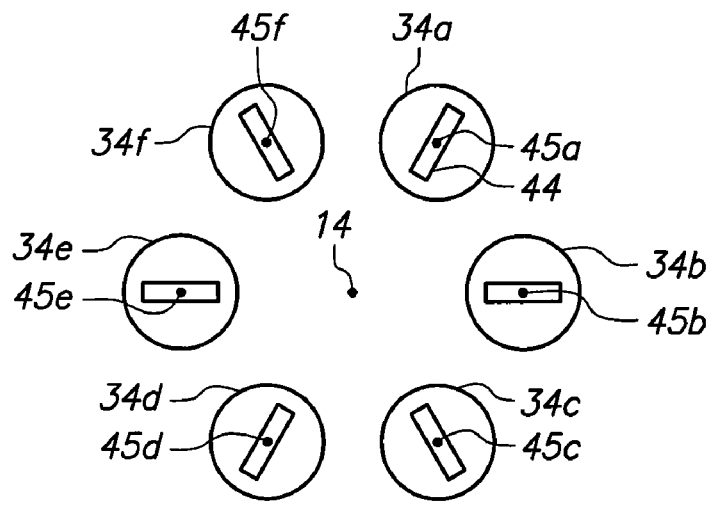
FIG. 6D is a cross-sectional view of an alternate embodiment for incisions.
Figure 6E:
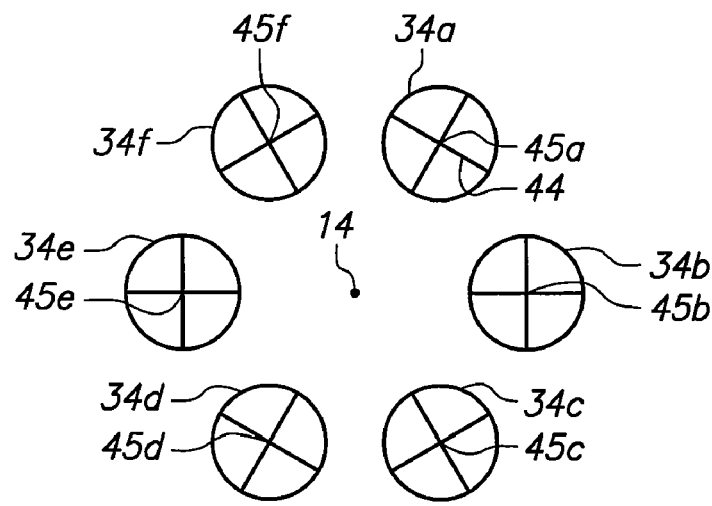
FIG. 6E is a cross-sectional view of an alternate embodiment for incisions.

As an alternative to the incisions 44 disclosed above, FIG. 6D indicates that incisions 44 may be created to form rectangular cylinders centered on the respective central axes 45. Similarly, FIG. 6E indicates that the incisions 44 may be created to form crosses centered on the respective central axes 45. As shown in FIGS. 6D and 6E, the rectangular cylinders and crosses are also aligned with the visual axis 14.

Figure 7:
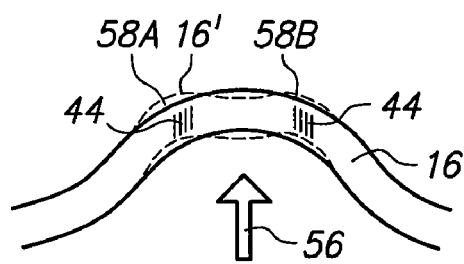
FIG. 7 is a cross-sectional view of a cornea showing the bio-mechanical consequence of making incisions in the cornea in accordance with the present invention.

FIG. 7 provides an overview of the bio-mechanical reaction of the cornea 16 when incisions 44 have been made in the operational volume 34 of the stroma 28. As stated above, the incisions 44 are intended to weaken the stroma 28. Consequently, once the incisions 44 have been made, the intraocular pressure (represented by arrow 56) causes a change in the force distribution within the stroma 28. This causes bulges 58a and 58b that result in a change in shape from the original cornea 16 into a new configuration for cornea 16', represented by the dashed lines. As intended for the present invention, this results in refractive corrections for the cornea 16 that improves vision.

While the particular System and Method for Correcting Higher Order Aberrations with Changes in Intrastromal Bio-mechanical Stress Distributions as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for correcting higher order aberrations in an eye, wherein the eye defines a visual axis and the method comprises the steps of:
    identifying at least one volume of stromal tissue in the eye, wherein the volume of tissue defines a central axis located at a distance from the visual axis of the eye and oriented substantially parallel thereto;
    focusing a pulsed laser beam to a focal spot in the volume of stromal tissue to cause Laser Induced Optical Breakdown (LIOB) of stromal tissue at the focal spot;
    moving the focal spot of the pulsed laser beam through the volume of stromal tissue to create a plurality of incisions centered about the respective central axis of the volume, to cause a predetermined selective weakening of the stroma for correction of the higher order aberration; and
    wherein each plurality of incisions forms concentric cylinders centered on the central axis.

2. A method as recited in claim 1 wherein a plurality of volumes of stromal tissue are identified, wherein a plurality of incisions are created about respective central axes, and wherein the respective central axes are equidistant from each other.

3. A method as recited in claim 1 wherein each volume of stromal tissue is bounded by Bowman's membrane and wherein each incision is at least ten microns from Bowman's membrane.

4. A method as recited in claim 3 wherein each volume of stromal tissue is further bounded by the endothelium and wherein each incision is at least 150 microns from the endothelium.

5. A method for correcting higher order aberrations in an eye, wherein the eye defines a visual axis and the method comprises the steps of:
    identifying at least one volume of stromal tissue in the eye, wherein the volume of tissue defines a central axis located at a distance from the visual axis of the eye and oriented substantially parallel thereto, and wherein each volume has an anterior surface located at least ten microns from Bowman's membrane and a posterior surface located approximately 150 microns from the endothelium of the cornea;
    focusing a laser beam to a focal spot in the volume of stromal tissue to cause Laser Induced Optical Breakdown (LIOB) of stromal tissue at the focal spot;
    moving the focal spot of the laser beam within the volume of stromal tissue to create at least one incision centered about the respective central axis of the volume, to cause a predetermined selective weakening of the stroma for correction of the higher order aberration; and
    wherein, for each volume of stromal tissue, a plurality of incisions are created to form concentric cylinders centered on the respective central axis.

6. A method as recited in claim 5 wherein a plurality of volumes of stromal tissue are identified, wherein at least one incision is created about each of the respective central axes, and wherein the respective central axes are equidistant from each other.

7. A method as recited in claim 5 wherein each volume of stromal tissue is bounded by Bowman's membrane and wherein each incision is at least ten microns from Bowman's membrane.

8. A method as recited in claim 7 wherein each volume of stromal tissue is further bounded by the endothelium and wherein each incision is at least 150 microns from the endothelium.

* * * * *